United States Patent
Zarkh et al.

(10) Patent No.: US 8,731,642 B2
(45) Date of Patent: May 20, 2014

(54) APPARATUS AND METHOD FOR LOCATING A DEVICE TIP WITHIN A VOLUME

(75) Inventors: Michael Zarkh, Giv'at Shmuel (IL); Rafael Shmuel Brada, Hod Hasharon (IL)

(73) Assignee: Paieon Inc. NY (US)

( * ) Notice: Subject to any disclaimer, the term of this patent is extended or adjusted under 35 U.S.C. 154(b) by 608 days.

(21) Appl. No.: 12/941,138

(22) Filed: Nov. 8, 2010

(65) Prior Publication Data

US 2011/0112398 A1 May 12, 2011

Related U.S. Application Data

(60) Provisional application No. 61/259,176, filed on Nov. 8, 2009.

(51) Int. Cl.
*A61B 5/05* (2006.01)

(52) U.S. Cl.
USPC .......... 600/426; 600/407; 600/424; 600/425; 382/128; 382/131; 382/132; 378/1; 378/4; 378/21; 378/62

(58) Field of Classification Search
USPC .......... 600/407, 425, 426, 424; 382/128, 131, 382/132
See application file for complete search history.

(56) References Cited

U.S. PATENT DOCUMENTS

| | | | | |
|---|---|---|---|---|
| 4,838,879 | A * | 6/1989 | Tanabe et al. | 604/529 |
| 6,285,903 | B1 * | 9/2001 | Rosenthal et al. | 600/433 |
| 6,490,474 | B1 * | 12/2002 | Willis et al. | 600/424 |
| 6,939,322 | B2 * | 9/2005 | Crank et al. | 604/117 |
| 8,014,849 | B2 * | 9/2011 | Peckham | 600/424 |
| 2006/0241413 | A1 | 10/2006 | Boese et al. | |
| 2007/0197905 | A1 | 8/2007 | Timinger et al. | |
| 2008/0043902 | A1 | 2/2008 | Viswanathanv | |
| 2008/0221440 | A1 * | 9/2008 | Iddan et al. | 600/424 |
| 2010/0217116 | A1 * | 8/2010 | Eck et al. | 600/424 |

* cited by examiner

*Primary Examiner* — James Kish
(74) *Attorney, Agent, or Firm* — Soroker-Agmon

(57) ABSTRACT

A method for determining by an x-ray projection a position of a target radiopaque marker disposed on a catheter in a subject's body, comprising assigning a landmark in the body as a reference point compensated for periodic movements of the body, determining an auxiliary location relative to the reference point using at least one additional radiopaque marker disposed on the catheter and based on the auxiliary location determining the position of the target radiopaque marker with respect to the reference point.

16 Claims, 10 Drawing Sheets

APPARATUS AND METHOD FOR LOCATING A DEVICE TIP WITHIN A VOLUME

BACKGROUND

The present disclosure generally relates to medical imaging, and more specifically to determining a position of a part of a catheter in a body.

In many applications, including Electro Physiology (EP) applications such as artificial pacemaker implantation, and the diagnosis and treatment of cardiac rhythm disorders, it is required to map the surface of a bodily cavity, i.e., to provide a geometrical description of the surface plane, and to identify the location of one or more blood vessels such as pulmonary veins entering or leaving the cavity.

An artificial pacemaker is a medical device which generates electrical impulses and delivers them by electrodes contacting the heart muscles, to regulate the heart beating. The primary purpose of a pacemaker is to maintain appropriate heart rate. A pacemaker may be required either because the hearts natural pacemaker is not fast enough, or there is a block in the heart's electrical conduction system. Pacemakers may be single, dual or triple chamber, i.e., contain one, two or three leads, respectively. Pacemakers may also include pacing, Implantable Cardioverter Defibrillator (ICD) or Cardiac Resynchronization Therapy (CRT).

Referring now to FIG. 1, showing a schematic illustration of an implanted exemplary pacemaker and its wires. Pacemaker 102 is implanted under the skin in the left upper chest area of the patient. The CRT is delivered as electrical pulses to the right and left ventricles of the heart through soft insulated wires which are inserted through the veins to the heart. The end of each lead is exposed and delivers pulses to the area which it is in contact with. In some applications the pacemaker comprises three leads, wherein end 104 of lead 108 is placed in the right atrium 112, end 116 of second lead 120 is placed in the right ventricle 124, and end 128 of third lead 132 is placed in tissues 136 surrounding left ventricle 140.

In order to place the lead ends so that the signals provide the best possible results, it is required to map parts of the heart, and in particular the right ventricle, so that once a location for the lead end is determined in the right ventricle, the lead can indeed be placed in that location, e.g., on the septum part of the Right Ventricle Outflow Tract (RVOT).

Additional applications that requires mapping of the chambers of the heart relate to mapping the electrical activity of the heart, including creating maps showing the relative timing of the electrical activities at different parts of the heart. Sometime mapping and treatment requires going through the septum between the right atrium to the left atrium mapping the right atrium may provide guidance for passing transseptally into the left atrium. In the left atrium the location of the pulmonary veins is of interest for many procedures both for diagnostic and for treatment purposes.

Some methods are known in the heart for mapping cavities, such as heart ventricles. One family of methods includes a 3-dimensional electromagnetic mapping system, which comprises one or more electromagnetic location pads positioned externally to the patient, and an electromagnetic sensor-equipped catheter. At each point the catheter provides its location according to the sensed magnetic field.

Another family of methods includes attaching three pairs of electrodes to the patient, wherein each pair is orthogonal to the other two pairs of electrodes, so as to cover the 3-dimensional space.

A mapping catheter is inserted into the body of a subject and placed adjacent to the mapped feature. The Voltage measured by the mapping catheter indicates the location of the measuring electrode along the dimension of the line connecting each pair of electrodes, which enables the determination of the three dimensional location of the measuring electrode.

However, each of these methods requires special equipment and procedures which are generally not available in operating rooms.

There is thus a need in the art for a method and apparatus for mapping bodily cavities with standard equipment available in operating rooms, and in particular X-ray imaging equipment. Although X-ray equipment provides two-dimensional images, yet it is required to obtain a three-dimensional mapping of the cavity such as a heart ventricle, by mapping an external surface thereof.

SUMMARY

One exemplary embodiment of the disclosed subject matter is a method for determining by an x-ray projection a position of a target radiopaque marker disposed on a catheter in a subject's body, comprising:

assigning a landmark in the body as a reference point compensated for periodic movements of the body;

determining an auxiliary location relative to the reference point using at least one additional radiopaque marker disposed on the catheter; and based on the auxiliary location determining the position of the target radiopaque marker with respect to the reference point.

Optionally or alternatively, the method comprises:

assigning a landmark in the body as a reference point;

determining an auxiliary location, compensated for periodic movements of the body, relative to the reference point using at least one additional radiopaque marker disposed on the catheter; and based on the auxiliary location determining the position of the target radiopaque marker, compensated for periodic movements of the body, with respect to the reference point.

Another exemplary embodiment of the disclosed subject matter is a method for determining by an x-ray projection a position of a target radiopaque marker disposed on a catheter in a subject's body, comprising:

assigning a landmark in the body as a reference point;

determining an auxiliary location, compensated for periodic movements of the body, relative to the reference point using at least one additional radiopaque marker disposed on the catheter; and based on the auxiliary location determining the position of the target radiopaque marker, compensated for periodic movements of the body, with respect to the reference point.

Yet another exemplary embodiment of the disclosed subject matter is a method for determining in an x-ray projection the direction of at least a part of a catheter having a longitudinal dimension, comprising:

projecting a catheter having at least one radiopaque marker shaped for manifesting the direction thereof with respect to an x-ray projection; and determining at least an asymmetry property of the at least one radiopaque marker as projected, thereby obtaining the direction of the part of the catheter in a vicinity of the at least one radiopaque marker with respect to the x-ray projection.

Yet another exemplary embodiment of the disclosed subject matter is a method for compensating a position of a landmark in a subject affected by periodic motions, comprising:

obtaining a multiplicity of images comprising a detectable marker disposed by the landmark at multiple phases within the at least one periodical motion;

modeling the motions of the landmark with respect to phases of the at least one periodical motion by determining a displacement of the position of the detectable marker due to at least one periodical cycle; and compensating for the motions of the landmark due to periodic motion in at least one image subsequently acquired at a phase of a periodic motion by applying an opposite displacement of the modeled displacement respective to the phase at the least one image subsequently acquired.

Yet another exemplary embodiment of the disclosed subject matter is a method for mapping a wall of a cavity in a subject's body affected by periodic movements, comprising:

acquiring a plurality of x-ray projections of a radiopaque marker touching the wall at a plurality of locations;

determining a plurality of spatial positions of the radiopaque marker with respect to a position of a landmark compensated for the periodic movements; and constructing the plurality of spatial positions into a spatial representation of the wall.

Yet another exemplary embodiment of the disclosed subject matter is a catheter having a longitudinal dimension and adapted for detecting a direction of at least a part thereof with respect an x-ray projection, the catheter comprising at least one radiopaque marker shaped for manifesting the direction thereof with respect to an x-ray projection.

For brevity and clarity and without limiting, in the present disclosure a reference to a point implies a position optionally within some margins or boundary due to limitations of the devices and/or computations.

BRIEF DESCRIPTION OF THE DRAWINGS

Some non-limiting exemplary embodiments of the disclosed subject matter are illustrated in the following drawings.

Identical or duplicate or equivalent or similar structures, elements, or parts that appear in one or more drawings are generally labeled with the same reference numeral, optionally with an additional letter or letters to distinguish between similar objects or variants of objects, and may not be repeatedly labeled and/or described.

Dimensions of components and features shown in the figures are chosen for convenience or clarity of presentation and are not necessarily shown to scale or true perspective. For convenience or clarity, some elements or structures are not shown or shown only partially and/or with different perspective or from different point of views.

Figure 1:
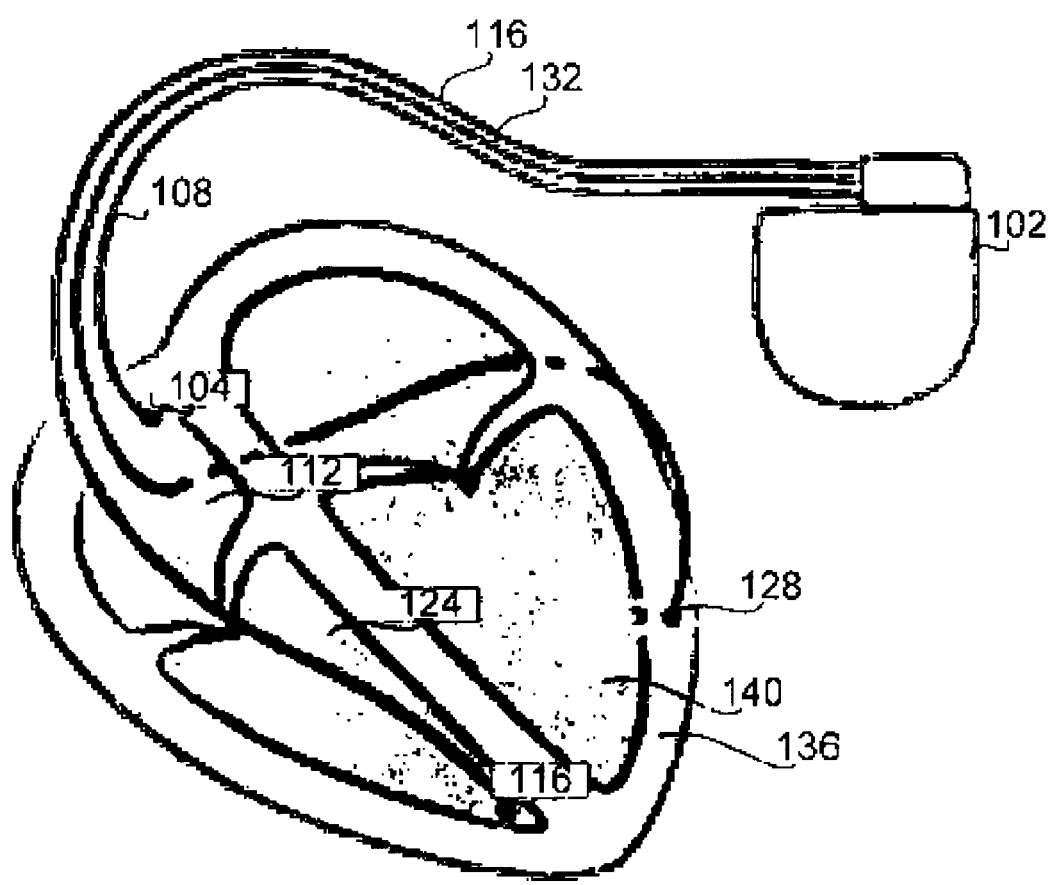
Figure 2:
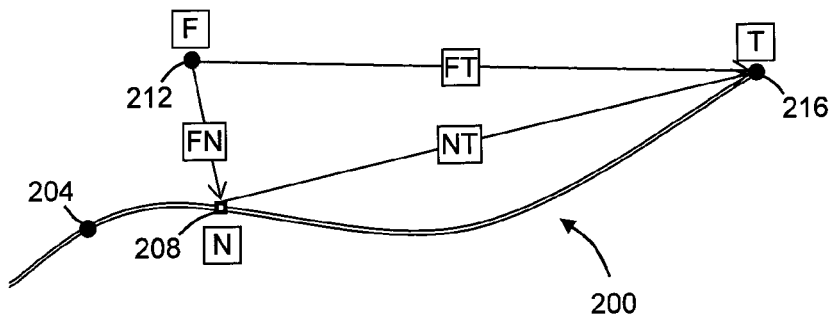
Figure 3:
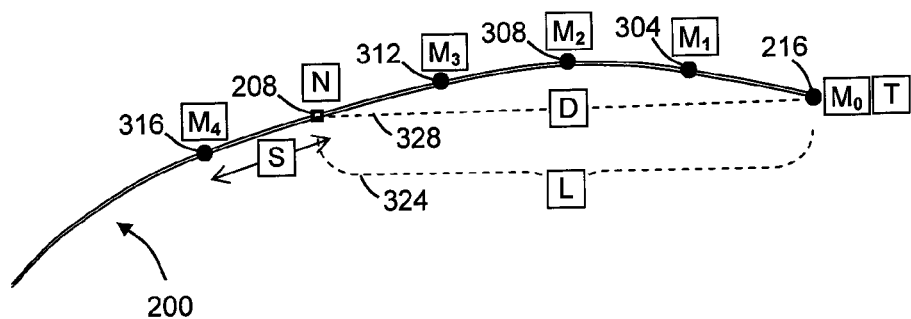
Figure 4:
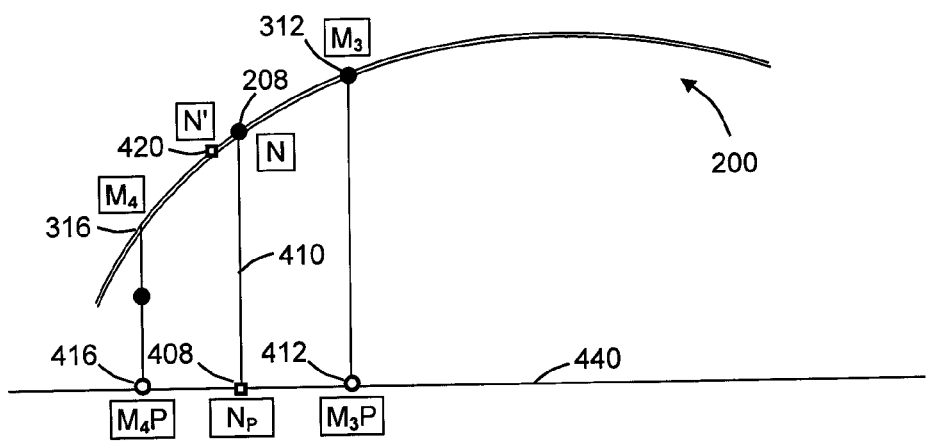
Figure 5:
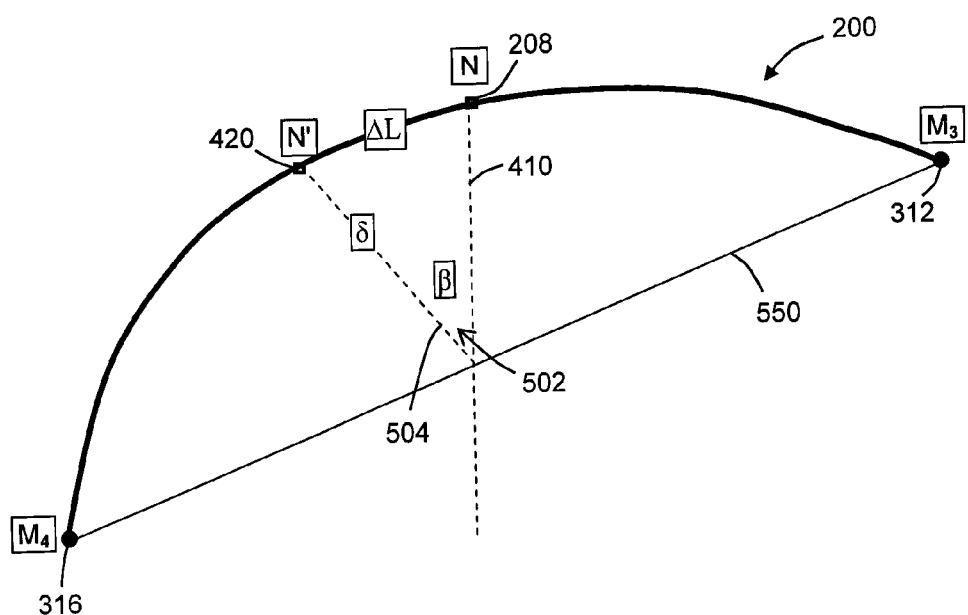
Figure 6:
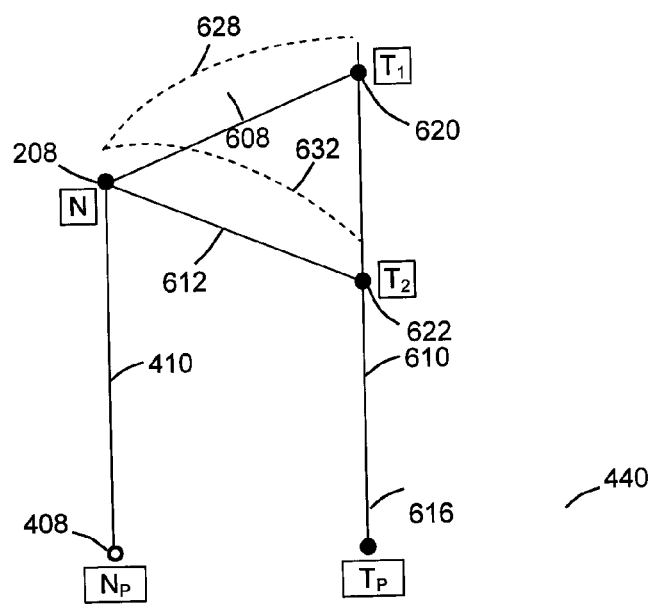
Figure 7A:
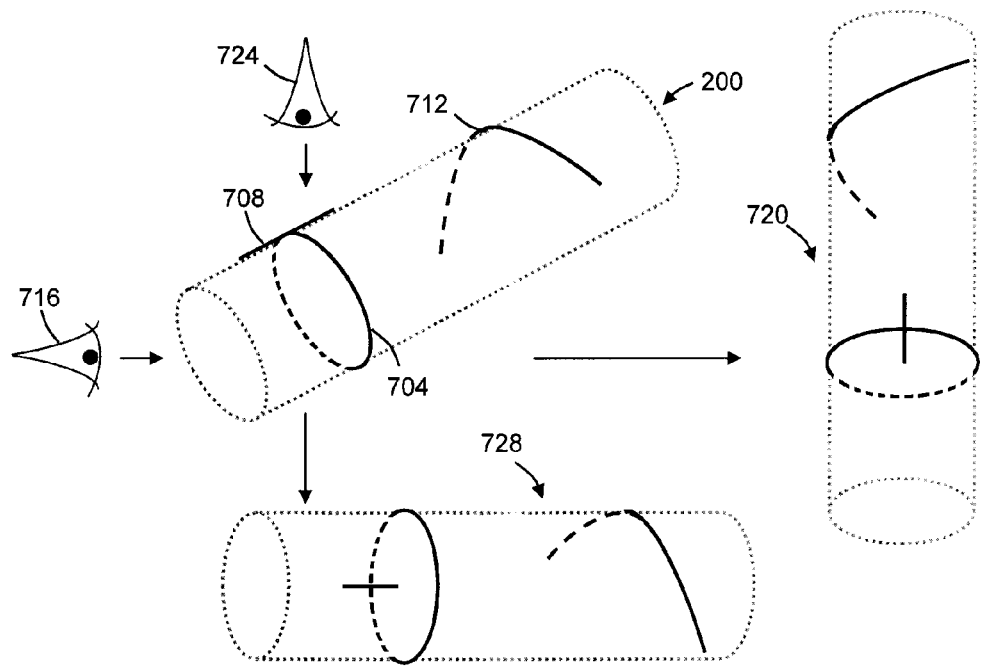
Figure 7B:
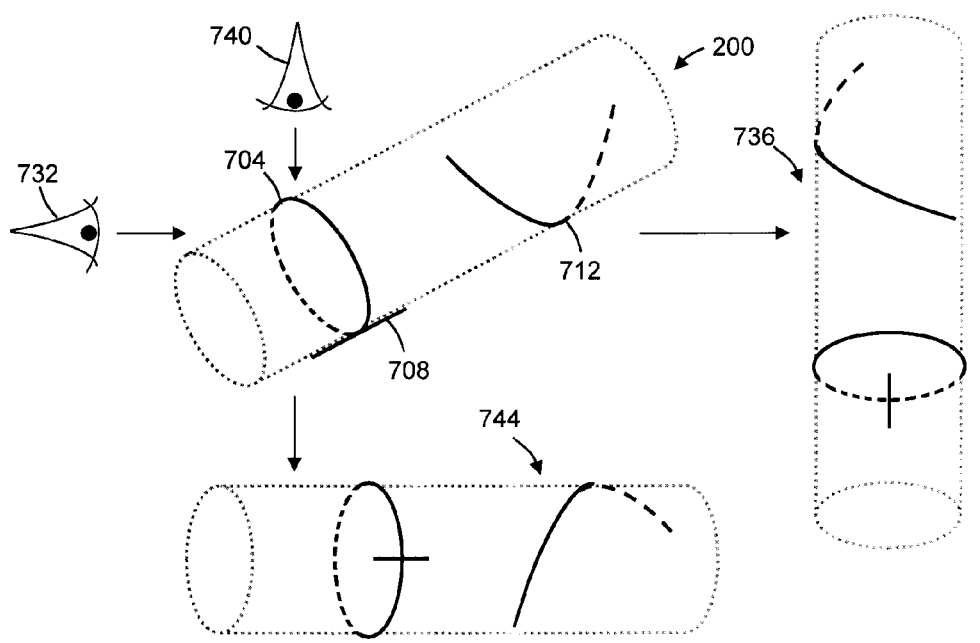
Figure 8A:
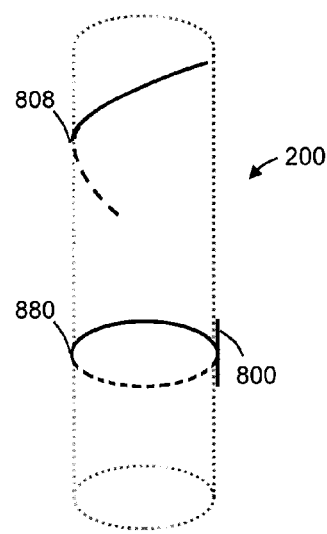
Figure 8B:
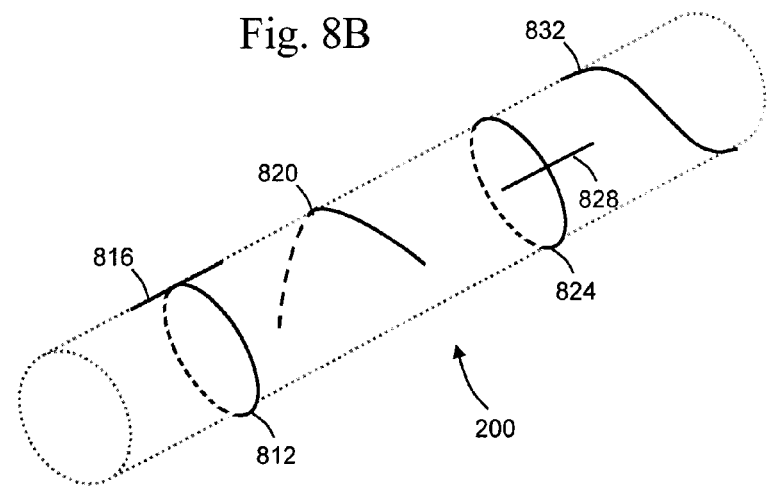
Figure 9:
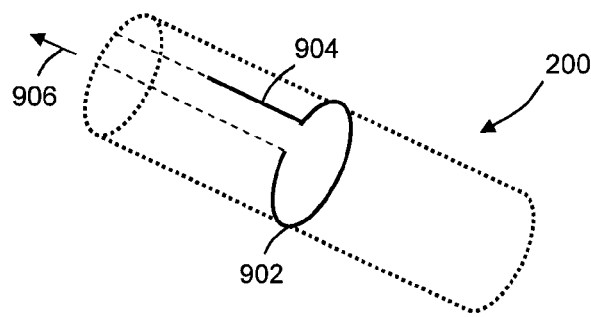
Figure 10A:
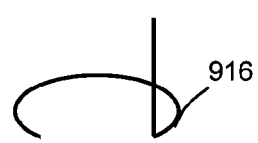
Figure 10B:
Figure 10C:
Figure 10D:
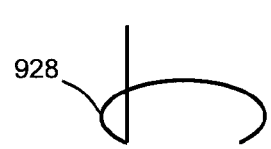
Figure 10E:
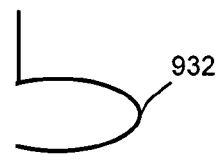
Figure 10F:
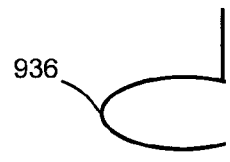
Figure 10G:
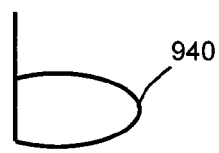
Figure 10H:
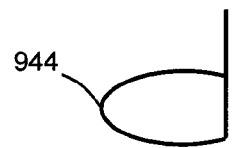
Figure 11:
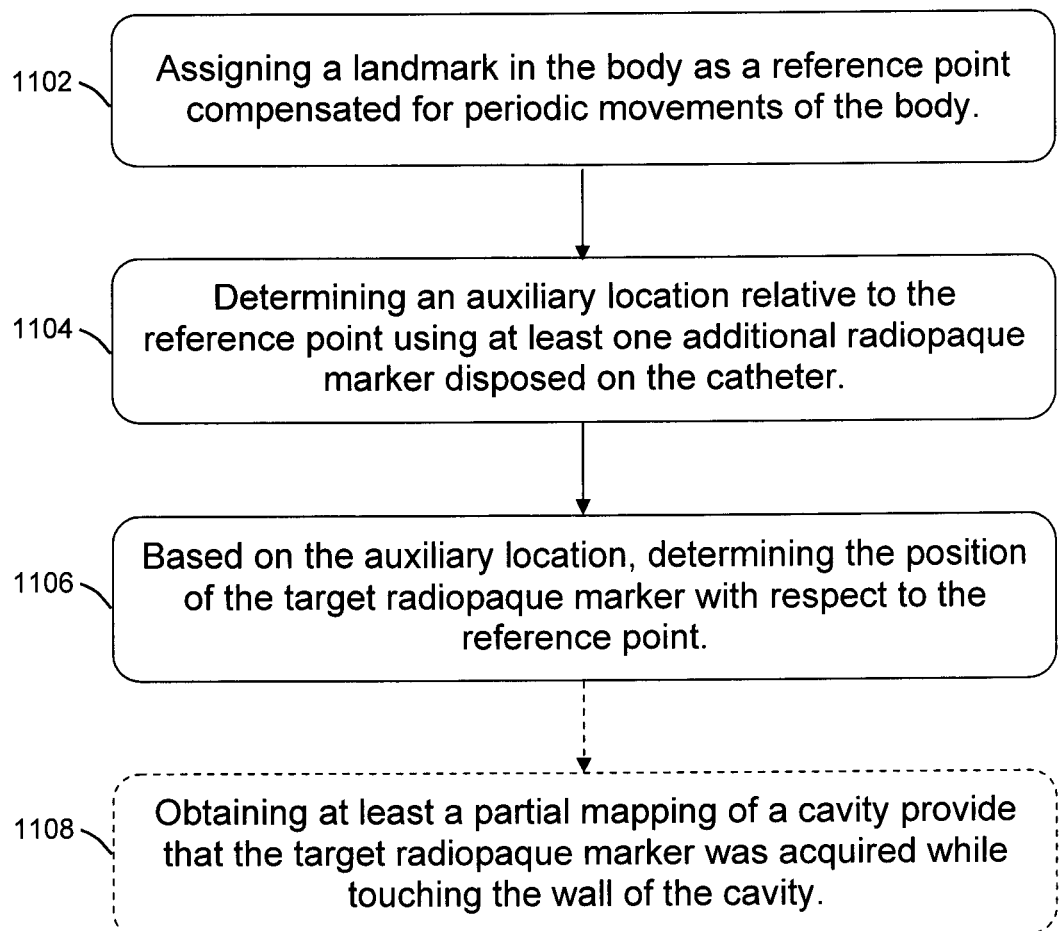
Figure 12:
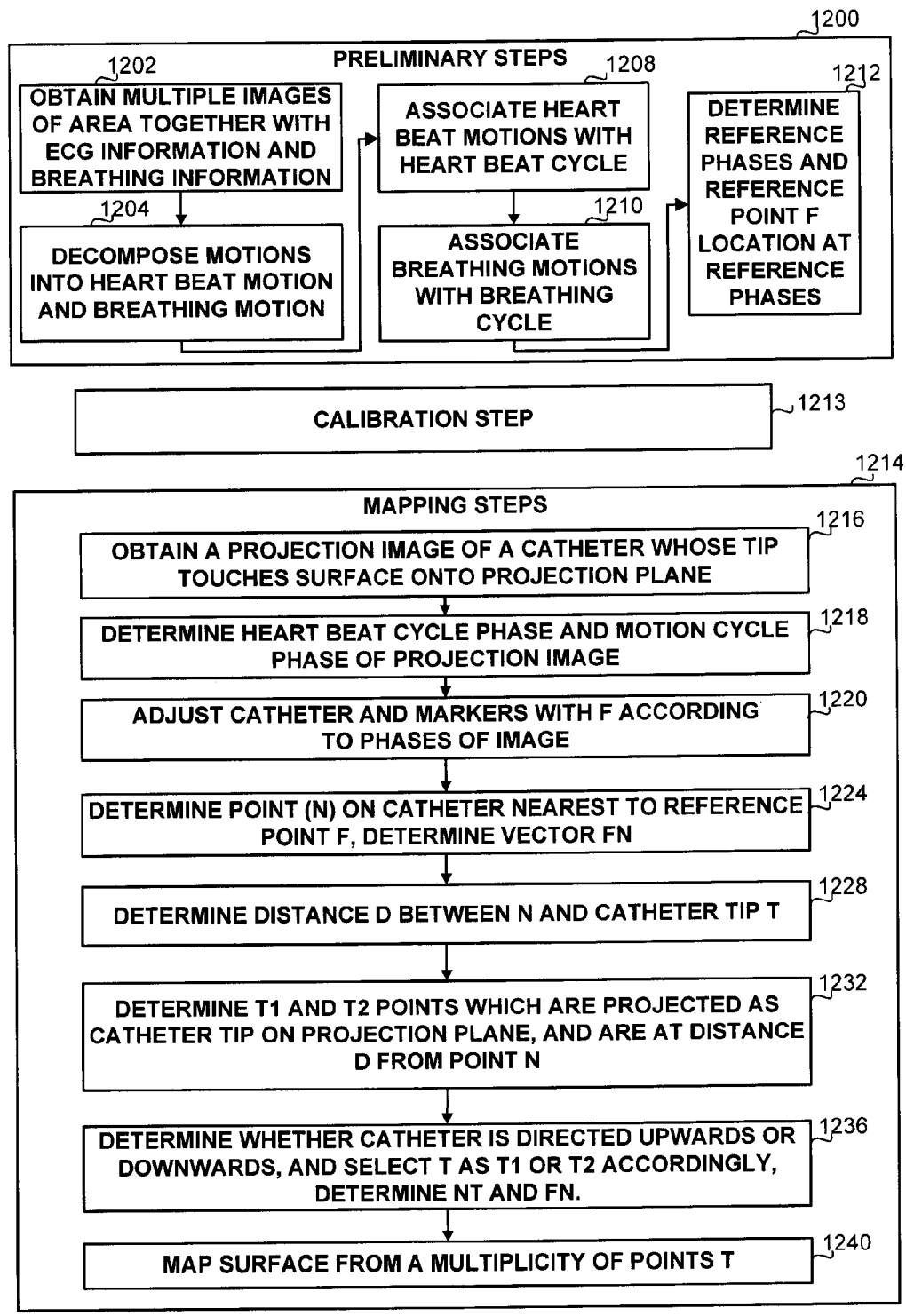
Figure 13A:
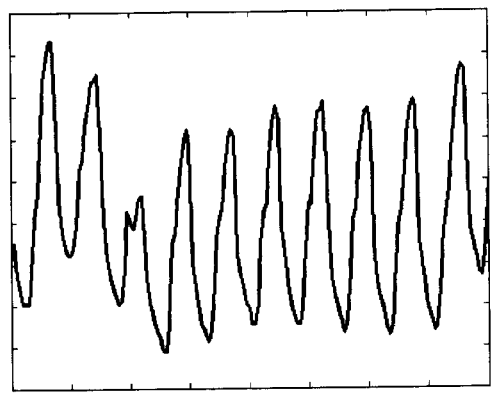
Figure 13B:
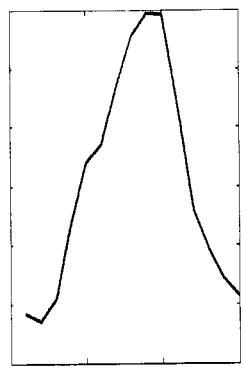
Figure 13C:
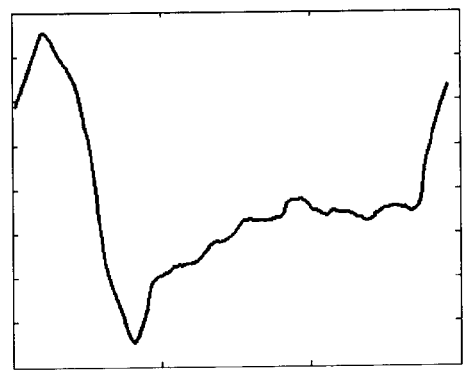
Figure 14:
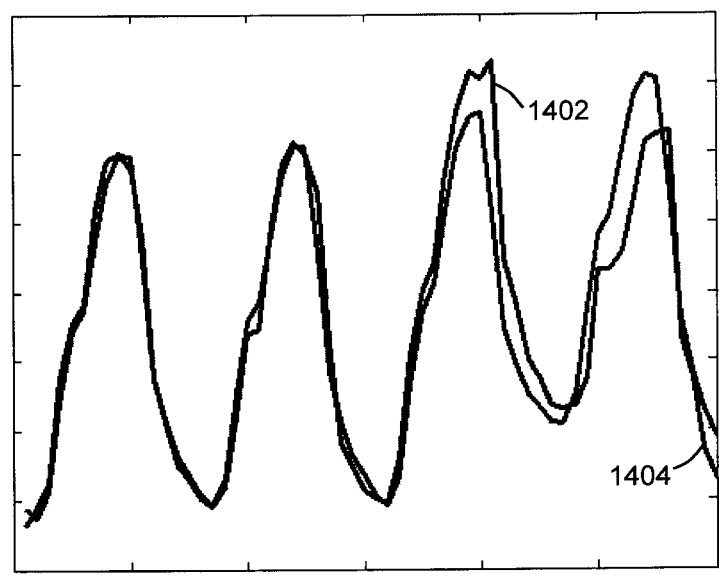

FIG. 1 is a schematic illustration of a heart with a pacemaker and leads thereof;

FIG. 2 is a schematic illustration of the general scheme for determining the location of a catheter tip, according to exemplary embodiments of the disclosed subject matter;

FIG. 3 is a schematic illustration of a catheter with distance markers, according to exemplary embodiments of the disclosed subject matter, according to exemplary embodiments of the disclosed subject matter;

FIG. 4 is a schematic illustration of a catheter with distance markers, as well as with its two-dimensional projection, according to exemplary embodiments of the disclosed subject matter;

FIG. 5 is a schematic illustration of a part of the catheter of FIG. 4, according to exemplary embodiments of the disclosed subject matter;

FIG. 6 is a schematic illustration of a catheter oriented in two directions in which the catheter tip has the same two-dimensional projection, according to exemplary embodiments of the disclosed subject matter;

FIGS. 7A and 7B illustrate schematic illustrations of catheters and possible respective projections, according to exemplary embodiments of the disclosed subject matter;

FIG. 8A schematically illustrates a projection of a catheter device, according to exemplary embodiments of the disclosed subject matter;

FIG. 8B shows a schematic illustration of a catheter with two sets of markers, according to exemplary embodiments of the disclosed subject matter;

FIG. 9 schematically illustrates a catheter equipped with a radiopaque marker of a shape and asymmetry for determination a direction, according to exemplary embodiments of the disclosed subject matter;

FIG. 10A-H schematically illustrates orientations of the marker of FIG. 9, according to exemplary embodiments of the disclosed subject matter;

FIG. 11 is a flowchart outlining of operations for determining a point of a catheter in a cavity, according to exemplary embodiments of the disclosed subject matter;

FIG. 12 is a flowchart of operations of a method for determining a point of a catheter in a cavity, according to exemplary embodiments of the disclosed subject matter;

FIG. 13A illustrates a combined signal of breathing and heart beats of a subject with respect to a certain dimension;

FIG. 13B illustrates a heart beat signal derived from the signal of FIG. 13A, according to exemplary embodiments of the disclosed subject matter;

FIG. 13C illustrates a breathing signal derived from the signal of FIG. 13A, according to exemplary embodiments of the disclosed subject matter; and FIG. 14 illustrates a combined signal of breathing and heart beats of a subject and a reconstructed signal of combined breathing and heart beats with respect to a certain dimension, according to exemplary embodiments of the disclosed subject matter.

DETAILED DESCRIPTION

The following description relates to one or more non-limiting examples of embodiments of the subject matter. The subject matter is not limited by the described embodiments or drawings, and may be practiced in various manners or configurations or variations. The terminology used herein should not be understood as limiting unless otherwise specified.

The disclosed subject matter is described below with reference to flowchart illustrations and/or block diagrams of methods, apparatus (systems) and computer program products according to embodiments of the subject matter. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks.

A general problem related with the present disclosure is mapping the walls of a cavity, such as a heart ventricle, in a body of a subject by generally planar projection of the cavity.

A general solution is using a catheter in the cavity and manipulating the tip of the catheter about the walls of the cavity, and detecting the tip position when the tip touches the wall.

It is noted that the tip of the catheter is used as an example of a convenient or practical part of the catheter, not precluding using other parts of locations of the catheter as a target location to be determined such as a marker on the catheter as a target marker. The term target implies, without limiting, a location sought for.

One technical problem dealt with by the disclosed subject matter is that the subject is moving such as by periodic movements of breathing and heart beats, thereby affecting the shape of the cavity.

Another technical problem is to determine the position of the catheter tip using conventional equipment typically present in operation rooms, such as x-ray imaging equipment, for example, x-ray fluoroscopy.

Yet another technical problem is to determine the three-dimensional position of the tip from generally planar representations, such as x-ray projections.

One technical solution is to locate or identify a landmark in the cavity or wall thereof or a landmark with known, up to a certain extent, relations with the cavity, and to use sensors or other equipment to identify the periodic movements of the subject and to compensate the position of the landmark for the periodic motions.

Another technical solution is to use radiopaque markers at particular locations in or on the catheter, enabling to identify the respective markers in the x-ray image. In the context of the disclosure, radiopaque do not necessarily imply a complete opacity but, rather, sufficient opacity for identifying a marker on the background of the subject anatomy in the x-ray image about the region of interest such as about or near the cavity.

Yet another technical solution is to use radiopaque markers and locations thereof about the catheter as projected in the x-ray image and to determine a three-dimensional position with respect to the movements-compensated position of the landmark, at least to certain or determined accuracy.

A potential technical effect of the disclosed subject matter is facilitating to insert devices such as catheter or electrode at known location in a subject cavity, and in particular non-limiting example, using x-ray imaging such as x-ray fluoroscopy.

For brevity and clarity and without limiting, unless otherwise specified, in the present disclosure a reference to a marker implies a radiopaque marker and/or a point represented by the marker according to the context.

A general non-limiting overview of practicing the present disclosure is presented below. The overview outlines exemplary practice of embodiments of the present disclosure, providing a constructive basis for a more detailed description of one or more embodiments and/or variant and/or alternative and/or divergent embodiments, some of which are subsequently described.

In some embodiments, on a preliminary stage, the periodical cycle or cycles of the subject's body area are studied. The cycles are studied both temporally and spatially, that is, it is determined how the phases of the breathing and the heart beat change the locations of points in the region of interest, for example, in the Superior Vena Cava (SVC) near the right atrium.

Subsequently, in some embodiments, the surface of the cavity is reconstructed by determining the location of a multiplicity of points on the surface. The determination is performed by inserting a catheter into the cavity, such that the catheter tip touches the surface. The surface is constructed by forming a grid of the locations of the multiplicity of points on the surface and optionally interpolating the grid with surfaces, such as by triangles, or otherwise representing or approximating the shape of the surface. In some embodiments, the surface representation is constructed with respect to a reference point described below.

During a learning stage, in some embodiments, the motions caused by breathing and heart beat cycles are studied. A marker, such as a fiducial point or a virtual landmark such as an anatomical feature or a marker is assigned, such as located or determined. For brevity and unless otherwise specified, the term landmark is collectively used for either the marker as a fiducial point or virtual landmark or any point or region which is located or determined as disclosed above. In some embodiments, the landmark location is selected such that the landmark is subject as much as possible only to movements caused by the abovementioned cycles and not to external motions. For example, the landmark can be selected or identified in the valve of the atrium, wherein movement is limited to one direction only.

In some embodiments, the landmark location is then tracked in a multiplicity of X-ray images or other images taken with the same projection parameters at different times throughout one or more heart beat cycles, wherein the heart beat cycles are determined by the motion of the landmark, by an electrocardiogram (ECG), or both. In some embodiments, additional and/or other methods can also be used for estimating the heart beat cycles such as by detecting the pulses of an artery. The landmark is identified in each image using image analysis techniques such as of the art of image processing. The landmark motion caused by the heart beat cycle is determined, and the total motion is decomposed or separated into two components: a component related to the heart beat cycle, and a component related to the breathing cycle. The separation of the motions is based, for example, on the difference of the period of heart rate and breathing using techniques such as band-pass filter or hi-pass and low-pass filter or Fourier transform.

FIG. 13A illustrates a combined signal of breathing and heart beats of a subject with respect to a certain dimension such as along a sagital plane, where the horizontal axis represents time and the vertical axis represents magnitude.

FIG. 13B illustrates a heart beat signal derived from the signal of FIG. 13A, where the horizontal axis represents a phase of a beat cycle along time and the vertical axis represents magnitude, according to exemplary embodiments of the disclosed subject matter.

FIG. 13C illustrates a breathing signal derived from the signal of FIG. 13A, where the horizontal axis represents the phase of the breath cycle along time and the vertical axis represents magnitude, according to exemplary embodiments of the disclosed subject matter.

FIG. 14 illustrates a combined signal 1402 of breathing and heart beats of a subject and a reconstructed signal 1404 of combined breathing and heart beats with respect to a certain dimension, according to exemplary embodiments of the disclosed subject matter.

It is noted that the combined signal 1402 was acquired independently of a signal used for decomposing heart beats and breathe, such as described with respect to FIGS. 13A-13B, for example, signal 1402 was acquired after the signal of FIG. 13A was acquired.

It is apparent that the combined signal 1402 and the reconstructed signal 1404 correlate with each other, demonstrating that a signal of breathing and heart beat is indeed formed as two additive components, namely, breathing and heart beat.

The reconstructed signal or phases thereof may be used, in some embodiments, for determining a reference point as described below.

In some embodiments, the motion caused by breathing is correlated with the breathing cycle. The breathing cycle can be obtained by an external breathing sensor, or by studying the movements of one or more features adjacent to the chest, such as ribs, diaphragm, or markers attached to chest, stitches, or the like.

Determining the effect of the breathing and the heart beat cycles on the relevant area itself rather than by external measures in some embodiments or cases, eliminates errors caused by determining such movements from a distance. The breathing sensor or the ECG equipment are thus, in some embodiments, used solely for determining the phase during the cycle, while the magnitudes of the movements are determined by detecting the landmark in the relevant area, that is, close to the heart.

Since the breathing cycle is generally longer than the heart beat cycle such as by an order of magnitude, that is about 10 times longer, then the movements caused by the heart beat cycle may be studied during the static phase of the breathing cycle. Since it is assumed that the movements caused by the two cycles are additive in nature, at least to a certain extent, the two cycles of breathing and heart beats may be determined independently, and the movements caused by the heart beat cycle may be accordingly compensated when estimating the movements caused by the breathing cycle.

In some embodiments, once the motions as correlated with the respective cycles of breathing and heart beats are determined, the location of the landmark in a pair of reference phases is selected as a reference point, denoted also as point F. In some embodiments, movements of the reference point subject to each phase of the heart beat cycle and each phase of the breathing cycle are also determined.

In some embodiments, the preliminary stage enables the determination of the coordinates of the landmark in a moving organ subject to one or more periodic cycles, by obtaining a multiplicity of images with a visible object located at the position of the virtual landmark in the moving organ at multiple phases within a periodical cycle. In some embodiments, the movements of the visible object caused by the periodical cycle are analyzed, and a location of a reference point in a reference phase is determined. In some embodiments, the displacements caused to the reference point by a periodical cycle are determined. Subsequently, in some embodiments, a multiplicity of images is obtained, and for one or more images, the appropriate phase within the periodic cycle is determined and the coordinates of the virtual landmark in the given image are determined.

In some embodiments, the operations for determining the reference point may be performed for images taken in two or more different viewing directions, in order to obtain the three-dimensional coordinates of the virtual landmark.

Based on the preliminary stage described above, in some embodiments, the coordinates of a reference point in an X-ray taken at an arbitrary phase during the breathing and heart beat cycles are translated or converted into the coordinates of the same point on particular phases of the heart beat cycle and the breathing cycle.

Subsequently, in some embodiments, a calibration is performed for determining a calibration factor for the image; that is, analyzing the effect of the projection angle and other parameters on the image. The calibration can be done using any available method, such as measuring the size of a known object, for example, a catheter, or by using the geometrical data from the X-ray system which may be available as part of the communication protocol such as the DICOM information associated with the images.

In some embodiments, after the calibration is accomplished, a reconstruction stage of the cavity is performed. In some embodiments, the surface of the cavity is mapped by attaching a catheter tip to multiple points on the surface, determining the location of the points, and reconstructing the surface from the determined points. In some embodiments, the catheter is equipped or attached with radiopaque markers which are identified in an image, where, in some embodiments, the radiopaque markers are placed at known distances from each other along the catheter. In some embodiments, electrical signals from an electrode located near the tip of the catheter may be used for detecting when the catheter is touching the wall of the cavity.

In some embodiments, a radiopaque marker is attached at or about the tip of the catheter distally from the part of the catheter outside the subject's body or entry point of the catheter into the subject. The point at or about the distal tip of the catheter is denoted as a tip point or as T. In some embodiments, the position or coordinates of the tip point on the surface of the cavity are determined from a fluoroscopic and/or other x-ray image as described below. It is noted that a point respective to a marker may be determined such a by the opacity or density center or gravity of the marker or by any computational method such as a center of a circle bounding the region of the marker.

In some embodiments, initially the phases within the heart beat cycle and the breathing cycle at which the image was obtained, as describe above, are determined. The heart beat phase can be determined, for example, using an ECG, or from the motion identified in a sequence of images, and the breathing phase can be determined, for example, by an external sensor, or by the location of a feature such as the ribs as described above.

Subsequently, in some embodiments, a displacement vector is composed or formed by adding the displacement caused by each cycle relevant to the reference phases.

The catheter and radiopaque markers thereon are located in the image using, for example, image analysis techniques.

In some embodiments, the relative location of the catheter markers and the reference point F are adjusted or modified by applying the displacement vector associated with the relevant phases in the cycles to the catheter locations such as points thereon and the markers attached thereon, or by applying the opposite or reversal of the displacement vector to reference point F thereby modifying or adjusting the position of reference point F.

Thus, in some embodiments, a learning and usage of periodic motions of a subject may be described additionally or alternatively as obtaining a multiplicity of images comprising a detectable marker disposed by the landmark at multiple phases within the at least one periodical motion and modeling the motions of the landmark with respect to phases of the at least one periodical motion by determining a displacement of the position of the detectable marker due to at least one periodical cycle. In a later usage compensating for the motions of the landmark due to periodic motion in at least one image subsequently acquired at a phase of a periodic motion by applying a displacement according to the modeled displacement respective to the phase at the least one image subsequently acquired. Optionally, the at least one image subsequently acquired comprises a plurality of images subsequently acquired at one or more phases of a periodic motion. Optionally, the detectable marker is a radiopaque marker detectable in x-ray imaging.

In some embodiments, after adjusting the catheter with the reference point, an auxiliary point on the catheter, denoted also as point N or N', is determined to aid in determining the location of the tip of the catheter and to provide a sufficient or increase the accuracy or the tip location relative, for example, to using other locations on the catheter and/or using the reference point F directly.

In some embodiments, preferably and without limiting, point N is nearest to the reference point F as possible. Additionally, without limiting, point N is located on a part of the catheter disposed in a blood vessel near the cavity so that point N is constrained, at least to a certain extent, in motions thereof and provides a rather stable basis relative, for example, to a point or marker on the catheter inside the cavity. In some embodiments, the motion of point N is restricted to the projection plane preventing or avoiding motion outside the projection plane such as in the direction of the projection. Thus, in some embodiments, as movements of N are constrained to a blood vessel, complications due to curvature of the catheter are reduced relative to locations outside the blood vessel, for example, in the cavity.

In the description below, without limiting the scope of the disclosure, point N is assumed to be in a blood vessel and nearest to the reference point F. It is also noted that point F, contrary to radiopaque markers, is a virtual point determined by computations and may be determined between any markers, yet not precluding that point N coincides with or overlaps or defined as a marker, for example, as a marker disposed on the catheter in the blood vessel.

Subsequently, in some embodiments, the location of catheter tip, denoted as tip point T or tip T or T, is determined using reference point F and the vector FT, which is the vector sum of FN and NT, that is, FT=FN+NT, wherein all vectors are in the 3-dimensional space. In the present disclosure a vector between two points is represented as a pair of letters denoting the points, for example, FN is a vector from F to N.

Vector FN is determined from the locations of F and N on the image, and using the imaging geometry, which is known from the imaging parameters at which the image was obtained, and from the calibration factor determined above.

An exemplary non-limiting embodiment of determination of NT is described below. Since the cavity enables maneuvering and moving the tip of the catheter in various directions, the direction of the tip of the catheter about the tip has to be determined. Namely, it is required to determine whether the catheter turns up or down at a vicinity of the tip. In the context of the present disclosure, unless otherwise specified, upwards indicates that the catheter tip is closer to the image viewer than the markers on the catheter, and downwards indicates that the catheter tip is farther from the viewer than the markers.

In some embodiments, the direction is determined by providing a combination of one or more radiopaque markers on the catheter, and by analyzing the two-dimensional projection of the markers.

Once a multiplicity of points such as point T is determined, the surface of the cavity wall can be mapped. The mapping enables, among others, the placement of a lead tip or an electrode at a desired location.

With reference to FIGS. 2-5, exemplary determination of NT vector is described below. It is noted that for clarity a point or other entities such as lines are designated by a symbol and referred to by the symbol in addition or instead a corresponding label or designation of the entity. For example, in FIG. 2 a point 212 may be referred to as point F or F'. It is also noted that in the drawings a catheter is schematically illustrated by a section thereof.

Referring now to FIG. 2, showing the general scheme of determining the location of the catheter tip, according to exemplary embodiments of the disclosed subject matter.

Catheter 200 has a longitudinal dimension, or axis, and comprises a number of radiopaque markers such as represented by a marker 204, and a tip point T represented by a marker 216. As, in some embodiments, the X-ray is image is acquired when the tip touches the surface being mapped, it is required to determine the location of tip 216.

A point 212 is the reference point F for which the movements caused by the heart beat and breathing cycles are determined in the preliminary stage.

The phase within the heart beat cycle and the phase within the breathing cycle at which the image was obtained are determined. Accordingly, the catheter and markers thereof are adjusted with reference point 212 by applying the relevant displacement expected for reference point 212 at the phases within the cycles when the images are acquired. Alternatively, in some embodiments, reference point 212 is adjusted or modified by applying the reverse or opposite displacement.

A point 208 is selected as auxiliary point N on catheter 200 where point N is closest to reference point 212 as adjusted for the periodic movement of the subject.

In order to determine the location of point 216, the vector FT is determined as FT=FN+NT as illustrated in FIG. 2.

In some embodiments, the scheme of FIG. 2 and subsequent respective operations as described with respect to subsequent figures below is repeated for multiple locations of tip point T, wherein point T is assumed to be on the cavity wall surface for mapping the wall of the cavity.

Referring now to FIG. 3, showing a schematic illustration of the method for estimating the length of vector NT, according to exemplary embodiments of the disclosed subject matter.

FIG. 3 illustrates catheter 200 with tip point T as point 216, where for convenience point T and the catheter has a radiopaque marker at the tip thereof indicated as a marker $M_0$. Catheter 200 also comprises additional markers such as marker $M_1$ denoted as point 304, $M_2$ denoted as point 308, $M_3$ denoted as point 312 and $M_4$ denoted as 316, where the number of markers is provided as a non-limiting example. In some embodiments, the distances between every two markers are known. For simplicity and without limiting, it is assumes that the distance between every two neighboring markers is S where, for example, S is 10 mm.

As exemplified in FIG. 3, point 208 as auxiliary point N is located between $M_3$ and $M_4$. Assuming that the shape of catheter 200 between point N and point $M_0$ is linear, the distance 324 denoted as distance L or L between point N and point $M_0$ is estimated as:

$$L = 3*S + (N-M_3)/(M_4-M_3)*S, \text{ or according to the example:}$$

$$L = 30 \text{ mm} + (N-M_3)/(M_4-M_3)*10 \text{ mm}.$$

In some embodiments, for every known and/or constant shape of catheter 200 between point N and point $M_0$, a function denoted as 'g' can be determined, at least for sufficient accuracy, which relates distance L and straight distance 328 between point N and point $M_0$ where straight distance 328 is denoted as distance D or D, that is, $D = g(L)$.

In some embodiments, if catheter 200 is straight, at least between N and T then $D=L$, or if catheter 200 is straight, at least between M3 and T, or between $M_3$ and $M_4$, then $D \approx L$. Otherwise, function g can be formulated as a mathematical function or as a tabular function. The error in estimating D depends, in some embodiments, on the shape curvature of catheter 200 and/or on the orientation of the catheter relative to the imaging direction.

Referring now to FIGS. 4 and 5, demonstrating the error caused by the curvature and orientation of catheter 200 with reference to FIG. 3, according to non-limiting exemplary embodiments of the disclosed subject matter.

FIG. 4 illustrates catheter 200 and markers in known distances S. Makers M3 and M4 and point N are projected on an imaging plane 440 as point 412 denoted as point $M_3P$, point 416 denoted as point $M_4P$ and point 408 denoted as point Np, respectively, where an exemplary projection direction or ray is indicated as projection ray 410.

However, due to the curvature of catheter 200, the distance of point Np with relation relative to point $M_3P$ and point $M_4P$, or the proportions thereof, are different along catheter 200 with respect to point N and point $M_3$ and $M_4$.

In order to establish a point on catheter 200 with the same proportion as point. Np relative to point $M_3P$ and point $M_4P$, a point N' 420 corresponding to point Np is determined along catheter 200 that is in distance proportions with respect to point $M_3$ and M4 as the relations of point Np with relative to point $M_3P$ and point $M_4P$. for example, if point Np was exactly in the middle between point $M_3P$ and point $M_4P$, due to the curvature of catheter 200 point N is not exactly in the middle between point $M_3$ and M4, and point N' 420 is determined exactly between point $M_3$ and M4 on catheter 200.

Referring now to FIG. 5 that illustrates the position, or a deviation denoted as $\Delta L$ of point N' 420 with respect to point N, according to exemplary embodiments of the disclosed subject matter.

A foreshortening angle 502, denoted as β and a segment 504, denoted as δ, are formed by drawing an imaginary line 504 perpendicular to catheter 200 so that line 504 intersects with an imaginary line 550 drawn between $M_3$ and $M_4$ and with projection ray 410 that projects point N on imaging plane (such as 440 of FIG. 4). Thus $\Delta L$ is determined as $\Delta L = \delta * \tan(\beta)$ and, correspondingly, N' 420 is determined at a distance $\Delta L$ from N3, or for that matter, where line 504 begins on catheter 200.

The error in determining a position of point N due to curvature of the catheter, or the difference between distance D (of FIG. 4) and distance L, is effected at least partially by $\Delta L$. Thus, in some embodiments, some solutions may be used in order to avoid or reduce the magnitude of $\Delta L$. In some embodiments, one of the markers such as $M_3$ or $M_4$ is used as point N. In some other embodiments, $\Delta L$ can be determined sufficiently accurately for determining the position of point T by compensating the foreshortening effect of the x-ray projection image. Such compensation is possible because the angle between the projection image and the catheter is known. In yet some other embodiments, a catheter can be used in which the segments between the markers are straight, and the required flexibility is provided at the markers such as by flexible members or pivots.

It is noted that the error in estimating D may be effected, among others, by the viewing direction of the x-ray image. The error increases as the angle between the catheter and the projection direction is smaller as the catheter is viewed along the longitudinal dimension thereof and the distance between the markers is smaller or some or all the marker may overlap relative to viewing by a larger angle.

Once length D of vector NT is determined, then in order to determine the position of tip point T, a sphere having a radius D may be required to be defined around point N. The location of catheter tip as point T can be obtained by intersecting the sphere with the projection ray passing through point Tp. However, such intersection provides two points, point $T_1$, and point $T_2$, though in distinct cases point $T_1$, and point $T_2$ may overlap or coincide.

FIG. 6 illustrates a catheter oriented in two directions in which the catheter tip has the same two-dimensional projection, according to exemplary embodiments of the disclosed subject matter.

FIG. 6, with a reference also to FIG. 2, illustrates the two possible solutions of $T_1$, and $T_2$ as point 620 and point 622, respectively. Point N is projected onto imaging plane 440 as point $N_p$. Point $T_1$ and point $T_2$ are points along a projection ray 610 connecting tip T and projection thereof as point 616, denoted also as point $T_p$ or $T_p$, onto imaging plane 440. Segment 608 and segment 612 represent the radius of the sphere of length D, and intersects projection ray 610. Thus, the catheter tip is viewed either at point $T_1$ or at point $T_2$, depending on whether the catheter is directed upwards as indicated by dotted line 628 or downwards as indicated by dotted line 632.

It is noted that since there is a definite correlation between a planar projection of a distance such as NT or FT and the corresponding spatial distance. Therefore, by virtually intersecting projection ray 610 with a spatial sphere, the spatial three-dimensional distance such as NT is obtained, up to resolving the geometrical ambiguity of the two points point $T_1$ or at point $T_2$ as described below by determining the direction or orientation of the catheter with respect to the planer projection or with respect to the viewing direction of the catheter.

Thus, in some embodiments, having a single planar projection of the catheter three dimensional position of the catheter tip is obtained relative to point N, and hence, as described above, relative to reference point F.

In some embodiments, having a plurality of planar projections from different angle provides more information of the spatial position and errors such as due to the curvature of the catheter can be reduced.

In some embodiments, in order to resolve or determine whether the catheter is directed upwards or downwards, the catheter is equipped with one or more specially formed radiopaque markers. The projection of the shape of the markers onto imaging plane 440 enables to resolve the direction of the catheter or the catheter tip.

In some embodiments, the catheter is equipped with one or more radiopaque markers attached to the catheter where the markers have particular shape and/or symmetry or asymmetry and relationship with each other that reflect or manifest the direction of the catheter, at least about or in the vicinity of the marker or markets, with respect to a planar projection thereof. Thus, in some embodiments, the projections of the radiopaque marker or markers on the imaging plane have different combinations of symmetry or asymmetry properties for rotation around the catheter longitudinal dimension, or axis, and tilting of the catheter with respect to the observer. Accordingly, a projection of the markers on the imaging plane provides an indication whether the catheter tip is directed upwards or downwards.

FIGS. 7A and 7B schematically illustrate catheters and possible respective projections, demonstrating how the direction of the catheter can be concluded from the relationships between the projections of the radiopaque markers, according to exemplary embodiments of the disclosed subject matter.

In an exemplary embodiment illustrated in FIG. 7A, catheter 200 is equipped with a radiopaque ring-shaped marker as ring 704 placed around the perimeter of catheter 200, and a generally straight radiopaque marker segment or a rod, as segment 708 placed, such that ring 704 crosses segment 708. Catheter 200 is also equipped with a helix-shaped radiopaque helix marker as helix 712, for convenience disposed at a distance from ring 704. It is assumed, without limiting, that helix 712 is disposed closer to the tip of catheter 200 than ring 704 and segment 708.

Supposing, without limiting, that catheter 200 is projected on the imaging plane from the direction indicated by eye 716, resulting in a projection as indicated by arrow 720, where the helix ascends from left to right as illustrated, and the segment is on the side of the ring that is closer to the helix. Consequently, the catheter tip is in the upward direction.

If, on the other hand, catheter 200 is projected from the direction indicated by eye 724, In an exemplary embodiment illustrated in FIG. 7B, supposing, without limiting, that catheter 200 is projected from the direction indicated by eye 732, resulting in a projection as indicated by arrow 736, where the helix ascends from right to left as illustrated, and the segment is on the side of the ring that is farther from the helix. Consequently the catheter is in the upward direction If, on the other hand, catheter 200 is projected from the direction indicated by eye 740, resulting in a projection as indicated by arrow 744, where the helix ascends from right to left as illustrated and the segment is on the side of the ring that is closer to the helix. Consequently the catheter tip is in the downward direction.

The general rule for determining the catheter direction from the radiopaque markers can be summarized in Table 1 below, in which each entry represents whether the catheter is in the upward or downward direction, assuming that the helix is closer to the tip than the ring. Whether the helix is indicated to ascend from left to right or from right to left, is determined when the catheter projection is vertical, as in projection 720 and projection 736. If the projection is horizontal as projection 728 and projection 744, the ascending direction is to be traversed.

TABLE 1

|  | Straight segment is on the side of the ring closer to the helix | Straight segment is on the side of the ring farther from the helix |
| --- | --- | --- |
| Helix ascends from left to right | Upward | Downward |
| Helix ascends from right to left | Downward | Upward |

In some embodiments, the described solution can be implemented in an incremental mode, by applying the solution to a sequence of intervals $NM_3$, $M_3M_2$, $M_2M_1$, and $M_1M_0$, instead of single long interval $NM_0$, where a pair of points represents an interval between the respective points. Optionally, in the incremental scheme each interval may be treated as a straight interval, providing, in some embodiments, calculations immune to possible distortions in the catheter shape caused by mechanical forces exerted by the chamber walls, at least to some extent.

Thus, based on the asymmetry properties of markers, such as ring 704, segment 708 and helix 712, and the distance therebetween or relative positions thereof, the direction of catheter 200 may be determined.

It will be appreciated that the same or similar technique can be applied to other shapes and combinations of the radiopaque markers, and is not limited to the disclosed combination of ring, segment and a helix. Other combinations may require other rules or functions for deducing the direction of the catheter, yet, in some embodiments, such rules are determined using geometrical analysis. For example, in some embodiments, a partial ring, that is, a ring in which one or more sections are missing, is used instead of the ring shaped-marker and the straight segment.

It will be appreciated that the radiopaque markers can also be used as the spaced markers such as marker $M_0$, $M_1$, $M_2$, $M_3$, or point $M_4$ described above. Alternatively, different sets of markers can be used for distance indications and for orientation indication.

Referring FIG. 8A schematically illustrates a projection of a catheter device, according to exemplary embodiments of the disclosed subject matter, with a reference to FIGS. 7A and 7B. The scheme described above with respect to FIGS. 7A and 7B may not work well when the projection of the generally straight segment coincides with the boundary of the catheter, so it cannot be determined whether projection 800 of the generally straight segment crosses the side of projection 804 of the ring which is closer to projection 808 of the helix, or the side of projection 804 of the ring farther from projection 808 of the helix.

In order to solve such ambiguities, in some embodiments, a catheter can be equipped with two sets of ring with a generally straight segment and a helix, placed in an angle other than 180° apart from each other. Such combination will ensure that at least one set of a ring and segment and a helix will provide definite determination of the direction of the catheter.

FIG. 8B shows a schematic illustration of a catheter with two sets of markers, according to exemplary embodiments of the disclosed subject matter.

Catheter 200 is equipped with a first ring as ring 812, a first generally straight segment as segment 816 and a first helix as helix 820. Catheter 200 is further equipped with a second ring as ring 824, a second generally straight segment as segment 828 and a second helix as helix 832, such that segment 816 and segment 828 are in an angle other than 180° from each other, and so are helix 820 and helix 832. Preferably, without limiting, the angle between segment 816 and segment 828, and helix 820 and helix 832 is about 90°.

Referring also to FIG. 6, once the orientation of the catheter is determined, it can be determined whether the catheter tip is at point $T_1$ or at point $T_2$ of FIG. 6 above, so that the location of the tip is resolved. In some embodiments, assuming that the tip touches the surface to be mapped, obtaining the position of a multiplicity of tip points enables mapping of the surface.

In some embodiments, another marker or markers may be used in order to determine the direction of the catheter with respect to the planar projection.

FIG. 9 schematically illustrates a catheter 200 equipped with a radiopaque marker or a combination of markers, of a shape and asymmetry for determination a direction, according to exemplary embodiments of the disclosed subject matter.

In some embodiments, catheter 200 is equipped with a radiopaque marker, denoted as ring 902, having a partial-ring or open ring shape having two ends and an opening therebetween and placed substantially around the perimeter of catheter 200. Catheter 200 is further equipped with a radiopaque generally straight segment or a rod, having two ends, denoted as segment 904, placed such that an end thereof touches one end of ring 902 in an orientation generally parallel to the longitudinal dimension of catheter 200 about or in the vicinity of the location of segment 904. Optionally, segment 904 is placed such that a location between the two ends thereof touches one end of ring 902 in an orientation generally parallel to the longitudinal dimension of catheter 200 about or in the vicinity of the location of segment 904.

In some embodiments, as a non-limiting example, segment 904 is positioned such that its end that touches ring 902 is farther from the catheter tip than its other end, the general direction of the catheter tip indicated by arrow 906.

For resolving the tip point T among point $T_1$ or point $T_2$ of FIG. 6 above, the rotation direction between segment 904 and 902 ring has to be decided and taken into account. As illustrated in FIG. 9, if segment 904 is to be moved into the ring opening, it is closer to rotate it in the counterclockwise direction than in the clockwise direction.

In some embodiments, ring 902 and segment 904 as two elements may be formed as one element. Although the two elements can be manufactured as a single piece, for clarity and without limiting, ring 902 and segment 904 are referred to as two elements since the symmetry or asymmetry properties thereof are different, so that the relations between projections of the two elements enable the determination of the catheter direction.

FIG. 10A-H that schematically illustrates orientations of the marker of FIG. 9, according to exemplary embodiments of the disclosed subject matter, is referred to below.

In some projections that can result from the combinations of ring 902 and segment 904, such as projections 916, 920, 924 and 928, the projection of segment 904 is positioned internally to the opening in the projection of ring 902. In these cases, the rule for determining the catheter direction from the radiopaque markers can be summarized in Table 2 below, in which each entry represents whether the catheter is in the upward or downward direction, assuming that the end segment 904 that touches ring 902 is farther from the catheter tip then the other end of segment 904.

TABLE 2

|  | The ring opening is on the upper part of the ring | The ring opening is on the lower part of the ring |
| --- | --- | --- |
| Straight segment is on the right-hand side of the ring opening | Downward (920) | Upward (916) |
| Straight segment is on the left hand side of the ring opening | Upward (924) | Downward (928) |

In other projections that can result from the combinations of ring 902 and segment 904, such as projections 932, 936, 049 and 944, the projection of segment 904 is positioned at an end of the projection of ring 902. In these cases, the rule for determining the catheter direction from the radiopaque markers can be summarized in Table 3 below, in which each entry represents whether the catheter is in the upward or downward direction, assuming that the end of segment 904 that touches ring 902 is farther from the catheter tip then the other end of segment 904.

TABLE 3

|  | The ring opening is on the left hand side of the ring | The ring opening is on the right hand side of the ring |
| --- | --- | --- |
| Straight segment touches the upper side of the opening | Downward (932) | Upward (936) |
| Straight segment touches the lower side of the opening | Upward (940) | Downward (944) |

The rules described by tables 2 and 3 can be summarized for the exemplary embodiment presented, as the following rule: if in the projection image, the side of the opening of ring 902 to which segment 904 is attached is located clockwise relatively to the other end—when passing through the opening rather than through the full part of the ring—then the catheter tip is tilted towards the observer, that is, the direction of the catheter oriented upwards.

As another illustration of the determination of catheter 200, when segment 9024 rotated clockwise through the opening of ring 902 for projections 916, 924, 936 and 940 then the catheter 200 is in an upward orientation, and otherwise for projections 920, 228, 932 and 944.

Thus, based on the symmetry and/or asymmetry properties of markers as ring 902 with segment 904 the direction of catheter 200 may be determined. It is noted that the term symmetry as used in the present disclosure implies, without limiting, also a lack of symmetry, that is, asymmetry, or a partial symmetry such as symmetry only for flipping.

It will be appreciated that according to the description above other markers or combinations thereof can be designed enabling to determine the direction or spatial orientation of a catheter or a part thereof from a planar projection of the markers, at least with respect to the projection plane and/or at least the direction or orientation of the part of the catheter about or in the vicinity of a marker or markers.

FIG. 11 is a flowchart outlining of operations for determining a point of a catheter in a cavity, according to exemplary embodiments of the disclosed subject matter.

At 1102 a landmark in the body as a reference point compensated for periodic movements of the body is assigned. For example, a radiopaque fiducial marker or a virtual landmark such an anatomic feature. The compensation for periodic movements of the body is carried out, for example, by determining the heart beats and breathing cycles of the subject and tracking the movements of the landmark due to the periodic movements and applying a reversing or opposite movement of the landmark thereby obtaining a virtually fixed position for the landmark.

At 1104 an auxiliary location relative to the reference point using at least one additional radiopaque marker disposed on the catheter is determined. In some embodiments, the auxiliary location is located about a part of the catheter near or nearest to the reference point and where the motion of the auxiliary location is restricted, such as in a blood vessel, where the restriction is preferably, without limiting, in the imaging plane prevention motion in a direction out of the projection plane or in the direction of the projection. In some embodiments, the auxiliary location is a virtual location determined such as by computations. Optionally or alternatively, the auxiliary location is located at or about a radiopaque marker on the catheter.

At 1106 the position of a target radiopaque marker with respect to the reference point is determined based on the auxiliary location.

In some embodiments, the target radiopaque marker is disposed at or about the tip of the catheter.

At 1108 at least a partial mapping of a cavity is obtained provided that the target radiopaque marker was acquired while touching the wall of the cavity.

In some embodiments, the mapping is obtained or constructed by combining the locations of the target radiopaque marker into a spatial representation or geometrical representation or a spatial grid or an interpolated spatial grid.

FIG. 12 is a flowchart of operations of a method for determining a point of a catheter in a cavity, according to exemplary embodiments of the disclosed subject matter.

The method generally comprises preliminary operations in a block denoted as 1200 for determining the periodical movement of the area, and mapping operations in a block denoted as 1214 for obtaining the position of a point on a catheter represented by the tip thereof, and optional consequential determination of locations of multiple points on a surface to be mapped and combining the multiplicity of points into a geometrical surface.

At 1202 of preliminary steps 1200, multiple images such as fluoroscopic images are obtained of a region of interest such as a cavity and surrounding tissues thereof, showing the catheter and a landmark such as a fiducial element or a radiopaque marker.

At 1204 motions of a marker on the catheter are analyzed, and decomposed into motions caused by the heart beat cycle and motions caused by the breathing cycle.

At 1208 the heart beat motions are associated with the relevant phase within the heart beat cycle, and at 1210 the breathing motions are associated with the relevant phase within the breathing cycle. The cycles can be determined, for example, using external sensors such as breathing sensor and electrocardiogram.

At 1012 reference phases within the heart beat cycle and the breathing cycle are determined, and the location of a reference point, denoted as F, at these reference phases is determined. For example, the location of a reference point such as a landmark or a marker. Thus, it is determined for each phase throughout the cycle, what is the displacement applied to the reference point, or vector, relatively to the location thereof at the reference phases.

At 1013 a dimensional calibration is performed for calibrating the images obtained from known orientation and/or perspective.

At 1016 a catheter is projected using an imaging modality such as an X-ray, optionally when the tip of the catheter is assumed to be touching the surface to be mapped.

At 1018, the phases at which the projection image was obtained within the heart beat cycle and within the breathing cycle are determined, using for example, external sensors or analyzing the locations of features such as a fiducial or an anatomic feature.

At 1020 various points along the catheter, such as markers along the catheter, are adjusted with respect to the reference point, in accordance with the displacements determined at 1012. The points are adjusted using the displacements associated with the phases within the heart beat cycle and the breathing cycle at which the image was obtained. Alternatively, the reference point is adjusted with the reverse displacement vector.

At 1024 a point denoted as N is determined in the projected image. The point is a point on the catheter which is closest to the catheter, after the catheter and the reference point were adjusted at 1020. A vector FN from F to N is determined, using the adjusted points and the calibration factor determined at 1013.

At 1028 a distance denoted as D between point N and the catheter tip is determined, using distance markers placed at known distances on the catheter.

At 1032 a point $T_1$ and a point $T_2$ as candidate for the position of the catheter tip projected onto the projection plane as the catheter tip are determined at distance D from point N.

The geometrical meaning or interpretation of point $T_1$ and point $T_2$ is the intersection of a sphere of radius D around point N and the projection ray of the catheter tip.

At 1036 the direction of the catheter at the vicinity of the tip is determined, that is, resolving whether the catheter is directed upwards or downwards with respect to the imaging plane. The catheter tip, denoted as T, is then selected as either point $T_1$ or point $T_2$ according to the direction of the catheter. The direction determination may be performed by using specifically shaped markers on the catheter, as discussed, for example, with respect to FIGS. 7A, 7B, 8A and 8B above. Once the vector NT from N to T is determined, the vector FT from F to T can be determined as FN+NT.

At 1040, after the positions of multiple points as T have been determined, the geometrical depiction or representation of a surface can be optionally determined provided that images where captured when the catheter tip was touching the surface.

In some embodiments, the methods described above for embodiments of the disclosed subject matter are carried out, at least partially, by one or more computerized apparatus executing one or more programs designed to carry out the methods, at least partially, and stored on a computer-readable medium and/or comprised in an electronic circuitry.

In some embodiments, the computerized apparatus comprises or constitutes a general purpose computing platform, which is in communication with or otherwise receives images from an imaging modality such as an X-ray imaging modality. The computing platform is equipped with one or more input and output devices, such as a display device, a keyboard, a pointing device such as a mouse, or others. The method may be implemented as interrelated sets of computer instructions, arranged such as functions, executable programs, modules, or libraries.

In some embodiments, the computerized apparatus is connected and/or linked with devices such as x-ray equipment, ECG equipment of other sensors or detectors. For example, image capturing device for an x-ray fluoroscopy, analog-to-digital converter for ECG signal, strain gage or thermal sensor for sensing breathing, or a storage device. In some embodiments, detection of radiopaque markers and analyzing the shape thereof in the projected image are carried out by program for image processing and/or image analysis algorithm implemented as programs stored on a computer-readable medium and/or comprised in an electronic circuitry.

It will be appreciated that the disclosed apparatus, method and device are exemplary only and that further embodiments can be designed according to guidelines and/or concepts of the disclosed subject matter. Thus, for example, different, additional or fewer components or operations can be used, different features can be used, or different rules can be applied.

The flowchart and block diagrams in the Figures illustrate the architecture, functionality, and operation of possible implementations of systems, methods and computer program products according to various embodiments of the present disclosed subject matter. In this regard, each block in the flowchart or block diagrams may represent a module, segment, or portion of program code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the disclosed subject matter. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As will be appreciated by one skilled in the art, the disclosed subject matter may be embodied as a system, method or computer program product. Accordingly, the disclosed subject matter may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present disclosed subject matter may take the form of a computer program product embodied in any tangible medium of expression having computer-usable program code embodied in the medium.

Any combination of one or more computer usable or computer readable medium(s) may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CDROM), an optical storage device, a transmission media such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wireline, optical fiber cable, RF, and the like.

Computer program code for carrying out operations of the present disclosed subject matter may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The corresponding structures, materials, acts, and equivalents of all means or step plus function elements in the claims below are intended to include any structure, material, or act for performing the function in combination with other claimed elements as specifically claimed. The description of the present disclosed subject matter has been presented for purposes of illustration and description, but is not intended to be exhaustive or limited to the disclosed subject matter in the form disclosed. Many modifications and variations will be apparent to those of ordinary skill in the art without departing from the scope and spirit of the disclosed subject matter. The embodiment was chosen and described in order to best explain the principles of the disclosed subject matter and the practical application, and to enable others of ordinary skill in the art to understand the disclosed subject matter for various embodiments with various modifications as are suited to the particular use contemplated.

It should be appreciated that the above described methods and apparatus may be varied in many ways, including omitting or adding steps, changing the order of steps and the type of devices used. It should be appreciated that different features may be combined in different ways. In particular, not all the features shown above in a particular embodiment are necessary in every embodiment of the disclosed subject matter. Further combinations of the above features are also considered to be within the scope of some embodiments of the disclosed subject matter.

It will be appreciated by persons skilled in the art that the present disclosed subject matter is not limited to what has been particularly shown and described hereinabove. Rather the scope of the present disclosure is defined only by the claims, which follow.

The invention claimed is:

1. A method for determining by an x-ray projection a position of a target radiopaque marker disposed on a catheter in a subject's body, comprising:

assigning a virtual landmark in the body as a reference point;

obtaining a multiplicity of images comprising a detectable marker disposed on the catheter;

determining an auxiliary location relative to the reference point using at least one additional radiopaque marker disposed on the catheter; and compensating for periodic movements of the body on the multiplicity of images using the virtual landmark;

obtaining two optional locations of the catheter tip based on the auxiliary location;

selecting a target radiopaque marker location from the two optional locations in which the catheter has the same projection on the multiplicity of images;

determining the position of the target radiopaque marker with respect to the reference point;

wherein the method is performed by a general purpose computer.

2. The method for determining by an x-ray projection a position of a target radiopaque marker disposed on a catheter in a subject's body according to claim 1, wherein the determining an auxiliary location comprises determining on the catheter a location nearest to the reference point.

3. The method for determining by an x-ray projection a position of a target radiopaque marker disposed on a catheter in a subject's body according to claim 1, wherein the determining an auxiliary location comprises determining on the catheter a location with restricted motion with respect to a projection direction.

4. The method for determining by an x-ray projection a position of a target radiopaque marker disposed on a catheter in a subject's body according to claim 1, wherein the determining an auxiliary location comprises determining a location on the catheter disposed in a blood vessel.

5. The method for determining by an x-ray projection a position of a target radiopaque marker disposed on a catheter in a subject's body according to claim 1, wherein the determining the position of the target radiopaque marker with respect to the reference point comprises determining a spatial position of the target radiopaque marker with respect to the reference point.

6. The method for determining by an x-ray projection a position of a target radiopaque marker disposed on a catheter in a subject's body according to claim 5, wherein the determining a spatial position of the target radiopaque marker with respect to the reference point comprises determining the direction of the catheter in a vicinity of the target radiopaque marker with respect to the x-ray projection.

7. The method for determining by an x-ray projection a position of a target radiopaque marker disposed on a catheter in a subject's body according to claim 6, wherein the determining the direction of the catheter in a vicinity of the target radiopaque marker with respect to the x-ray projection comprises determining at least one of an asymmetry property of a plurality of radiopaque markers on the catheter or a relative position between a plurality of radiopaque markers on the catheter.

8. The method for determining by an x-ray projection a position of a target radiopaque marker disposed on a catheter in a subject's body according to claim 6, wherein the determining the direction of the catheter in a vicinity of the target radiopaque marker with respect to the x-ray projection comprises determining an asymmetry property of a plurality of at least one radiopaque marker on the catheter.

9. The method for determining by an x-ray projection a position of a target radiopaque marker disposed on a catheter in a subject's body according to claim 1, wherein the target radiopaque marker disposed on a catheter is disposed at a tip of the catheter.

10. The method for determining by an x-ray projection a position of a target radiopaque marker disposed on a catheter in a subject's body according to claim 1, comprises obtaining a plurality of positions of the target radiopaque marker acquired when the target radiopaque marker touches a wall of a cavity of the subject's body thereby providing a spatial representation of the wall of the cavity.

11. The method for determining by an x-ray projection a position of a target radiopaque marker disposed on a catheter in a subject's body according to claim 1, wherein the reference point compensated for periodic movements of the subject's body is obtained by modifying the position of the reference point with a reverse displacement of determined periodic movements of the subject's body.

12. A method for determining, by an x-ray projection, a position of a target radiopaque marker disposed on a catheter in a subject's body, comprising:

assigning a virtual landmark in the subject's body as a reference point;

obtaining a multiplicity of images comprising a detectable marker disposed on the catheter;

determining an auxiliary location, relative to the reference point using at least one additional radiopaque marker disposed on the catheter;

compensating for periodic movements of the body on the multiplicity of images using the virtual landmark;

obtaining two optional locations of the catheter tip based on the auxiliary location;

selecting a target radiopaque marker location from the two optional locations in which the catheter has the same projection on the multiplicity of images;

determining the position of the target radiopaque marker, with respect to the reference point; and wherein the method is performed by a general purpose computer.

13. A method for determining in an x-ray projection the direction of at least a part of a catheter having a longitudinal dimension, comprising:

projecting an x-ray image containing a catheter having at least one radiopaque marker shaped for manifesting the direction thereof with respect to an x-ray projection;

obtaining a multiplicity of images comprising a detectable marker disposed on the catheter;

compensating for periodic movements of the body on the multiplicity of images using the virtual landmark;

obtaining two optional locations of the catheter tip based on the auxiliary location;

selecting a target radiopaque marker location from the two optional locations in which the catheter has the same projection on the multiplicity of images;

determining a direction of the part of the catheter in a vicinity of the at least one radiopaque marker with respect to the x-ray projection;

wherein the method is performed by a general purpose computer.

14. The method for determining in an x-ray projection the direction of at least a part of a catheter having a longitudinal dimension according to claim 13, wherein the least one radiopaque marker is shaped as an open ring having two ends with a generally straight rod attached to one end of the open ring in an orientation generally parallel to the longitudinal dimension of the catheter.

15. The method for determining in an x-ray projection the direction of at least a part of a catheter having a longitudinal dimension according to claim 13, wherein the at least one radiopaque marker comprises at least one radiopaque marker shaped as a ring with a generally straight rod attached to the ring in an orientation generally parallel to the longitudinal dimension of the catheter and at least one radiopaque marker shaped as a helix.

16. A method for mapping a wall of a cavity in a subject's body affected by periodic movements, comprising:
   acquiring a plurality of x-ray projections of a radiopaque marker touching the wall at a plurality of locations;
   determining a plurality of spatial positions of the radiopaque marker with respect to a position of a virtual landmark; and
   constructing the plurality of spatial positions into a spatial representation of the wall;
   obtaining a multiplicity of images comprising a detectable marker disposed on the catheter;
   compensating for periodic movements of the body on the multiplicity of images using the virtual landmark;
   obtaining two optional locations of the catheter tip based on the auxiliary location;
   selecting a target radiopaque marker location from the two optional locations in which the catheter has the same projection on the multiplicity of images;
   wherein the method is performed by a general purpose computer.

* * * * *